United States Patent
Sarkar et al.

(10) Patent No.: US 9,449,377 B2
(45) Date of Patent: Sep. 20, 2016

(54) IMAGING METHODS AND COMPUTER-READABLE MEDIA

(71) Applicant: The United States of America, as represented by the Secretary, Department of Health and Human Service, Bethesda, MD (US)

(72) Inventors: Susanta Kumar Sarkar, Rockville, MD (US); Ambika Bumb, Greer, SC (US); Keir Cajal Neuman, Bethesda, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 14/049,096

(22) Filed: Oct. 8, 2013

(65) Prior Publication Data

US 2014/0099007 A1 Apr. 10, 2014

Related U.S. Application Data

(60) Provisional application No. 61/711,702, filed on Oct. 9, 2012.

(51) Int. Cl.
*G06K 9/00* (2006.01)
*G06T 5/50* (2006.01)
(Continued)

(52) U.S. Cl.
CPC ............. *G06T 5/50* (2013.01); *G01N 21/6428* (2013.01); *G01N 21/6458* (2013.01); *G01N 21/6486* (2013.01); *G06K 9/00134* (2013.01); *G06T 5/003* (2013.01); *G06T 2207/10016* (2013.01); *G06T 2207/10056* (2013.01); *G06T 2207/10064* (2013.01); *G06T 2207/20182* (2013.01); *G06T 2207/20216* (2013.01); *G06T 2207/20224* (2013.01); *G06T 2207/30024* (2013.01)

(58) Field of Classification Search
None
See application file for complete search history.

(56) References Cited

U.S. PATENT DOCUMENTS

2011/0062957 A1\* 3/2011 Fu et al. .................... 324/307
2012/0155725 A1\* 6/2012 Bathe et al. ................ 382/128

(Continued)

OTHER PUBLICATIONS

Fu "Characterization and application of single fluorescent nanodiamonds as cellular biomarkers", PNAS Jan. 2007, pp. 727-732.\*

(Continued)

*Primary Examiner* — Weiwen Yang
(74) *Attorney, Agent, or Firm* — Kilpatrick Townsend & Stockton LLP

(57) ABSTRACT

One aspect of the invention provides an imaging method including: (a) acquiring a first fluorescent image of an object of interest impregnated with fluorescent nanodiamonds; (b) applying a magnetic field to the fluorescent nanodiamonds in order to decrease fluorescence of the fluorescent nanodiamonds; (c) acquiring a second fluorescent image of the object of interest; and (d) subtracting the second fluorescent image from the first fluorescent image to produce a resulting image. Another aspect of the invention provides an imaging method including: (a) applying a time-varying magnetic field to an object of interest impregnated with fluorescent nanodiamonds to modulate the fluorescence of the fluorescent nanodiamonds; (b) acquiring a plurality of fluorescent images of the object of interest; and (c) for each corresponding pixel in the plurality of fluorescent images, calculating a fluorescence intensity using a lock-in technique.

12 Claims, 14 Drawing Sheets

(51) Int. Cl.
  *G01N 21/64* (2006.01)
  *G06T 5/00* (2006.01)

(56) References Cited

U.S. PATENT DOCUMENTS

2012/0211670 A1* 8/2012 Choi et al. ............... 250/459.1
2012/0271176 A1* 10/2012 Moghaddam et al. ....... 600/476

OTHER PUBLICATIONS

Chapman, et al., "Background-free imaging of luminescent nanodiamonds using external magnetic field for contrast enhancement," *Optics Letters*, vol. 38, No. 11, pp. 1847-1849 (2013).

Igarashi, et al., "Real-Time Background-Free Selective Imaging of Fluorescent Nanodiamonds in Vivo," *Nano Letters*, vol. 12(11), pp. 5726-5732 (2012).

* cited by examiner

FIG. 3

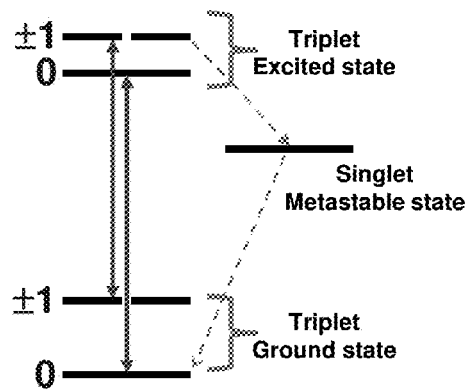
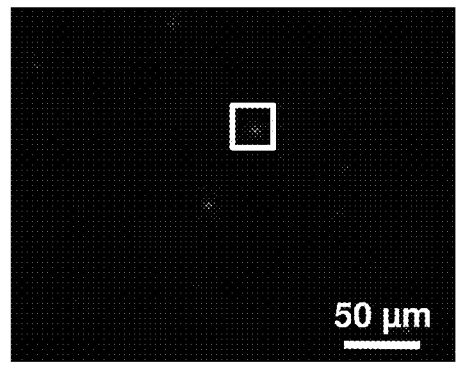
FIG. 7A
FIG. 7B
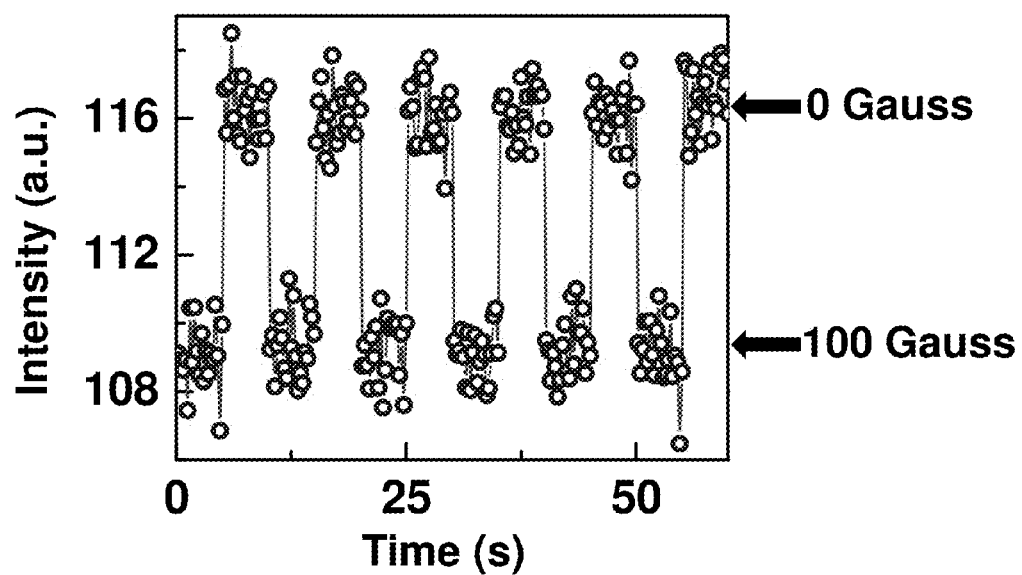
FIG. 7C

Lock-In ↑

IMAGING METHODS AND COMPUTER-READABLE MEDIA

CROSS-REFERENCE TO RELATED APPLICATIONS

This applications claims priority under 35 U.S.C. §119(e) to U.S. Provisional Patent Application Ser. No. 61/711,702, filed Oct. 9, 2012. The entire content of this application is hereby incorporated by reference herein.

STATEMENT REGARDING GOVERNMENTAL SUPPORT

The present subject matter was made with U.S. government support. The U.S. government has certain rights in this subject matter. This work was supported through grant number HL006087-02 BBC from the National Heart, Lung, and Blood Institute, National Institutes of Health.

BACKGROUND

Autofluorescence from naturally-occurring fluorescent biomolecules and fixative agents make it difficult to separate useful fluorescence from unwanted fluorescence due to overlapping emission spectra. Therefore, autofluorescence limits the capabilities of tissue and animal imaging. Even sophisticated spectral unmixing techniques cannot always reliably and accurately separate useful signal from background fluorescence.

SUMMARY OF THE PRESENT SUBJECT MATTER

One aspect of the invention provides an imaging method including: (a) acquiring a first fluorescent image of an object of interest impregnated with fluorescent nanodiamonds; (b) applying a magnetic field to the fluorescent nanodiamonds in order to decrease fluorescence of the fluorescent nanodiamonds; (c) acquiring a second fluorescent image of the object of interest; and (d) subtracting the second fluorescent image from the first fluorescent image to produce a resulting image.

This aspect can have a variety of embodiments. The object of interest can be a biological target. The biological target can be selected from the group consisting of: a cell, a plurality of cells, a tissue, an organ, and an organism.

The magnetic field can be generated by a permanent magnet. The magnetic field can be generated by an electromagnet.

The second fluorescent image can be acquired during application of the magnetic field.

Step (d) can be performed on a pixel-by-pixel basis.

The method can further include an additional step (e) of repeating steps (a)-(d) a plurality of times and averaging the resulting images. The plurality of times can be greater than 10.

Steps (a) and (c) can include applying an absorption wavelength to the object of interest.

Another aspect of the invention provides a non-transitory computer readable medium containing program instructions executable by a processor. The computer readable medium includes: (a) program instructions that acquire a first fluorescent image of an object of interest impregnated with fluorescent nanodiamonds; (b) program instructions that apply a magnetic field to the fluorescent nanodiamonds in order to decrease fluorescence of the fluorescent nanodiamonds; (c) program instructions that acquire a second fluorescent image of the object of interest; and (d) program instructions that subtract the second fluorescent image from the first fluorescent image to produce a resulting image.

This aspect can have a variety of embodiments. The second fluorescent image can be acquired during application of the magnetic field.

Another aspect of the invention provides an imaging method including: (a) applying a time-varying magnetic field to an object of interest impregnated with fluorescent nanodiamonds to modulate the fluorescence of the fluorescent nanodiamonds; (b) acquiring a plurality of fluorescent images of the object of interest; and (c) for each corresponding pixel in the plurality of fluorescent images, calculating a fluorescence intensity using a lock-in technique.

This aspect can have a variety of embodiments. The object of interest can be a biological target. The biological target can be selected from the group consisting of: a cell, a plurality of cells, a tissue, an organ, and an organism.

The magnetic field can be generated by a permanent magnet. The magnetic field can be generated by an electromagnet.

Step (b) can include applying an absorption wavelength to the object of interest. The plurality of fluorescent images can be acquired by a wide-field camera. The plurality of fluorescent images can be acquired by a confocal microscope.

Another aspect of the invention provides a non-transitory computer readable medium containing program instructions executable by a processor. The computer readable medium includes: (a) program instructions that apply a time-varying magnetic field to an object of interest impregnated with fluorescent nanodiamonds to modulate the fluorescence of the fluorescent nanodiamonds; (b) program instructions that acquire a plurality of fluorescent images of the object of interest; and (c) program instructions that, for each corresponding pixel in the plurality of fluorescent images, calculate a fluorescence intensity using a lock-in technique.

Another aspect of the invention provides an imaging method including: (a) applying an absorption wavelength to an object of interest impregnated with fluorescent nanodiamonds; and (b) after a delay of at least at least about 6 nanoseconds, acquiring a fluorescent image of the object of interest.

This aspect can have a variety of embodiments. The object of interest can be a biological target. The biological target can be selected from the group consisting of: a cell, a plurality of cells, a tissue, an organ, and an organism.

The delay can be greater than about 10 nanoseconds. The delay can be greater than between about 10 nanoseconds and about 20 nanoseconds.

The absorption wavelength can be generated by a pulsed laser. The absorption wavelength can be between about 450 nm and about 650 nm or between about 900 nm and about 1300 nm. The absorption wavelength can be between about 450 nm and about 650 nm or between about 850 nm and about 1350 nm.

Another aspect of the invention provides an imaging method including: (a) applying an absorption wavelength to an object of interest impregnated with fluorescent nanodiamonds; and (b) after a delay of at least at least about 4 nanoseconds, acquiring a fluorescent image of the object of interest.

This aspect can have a variety of embodiments. The object of interest can be a biological target. The biological target can be selected from the group consisting of: a cell, a plurality of cells, a tissue, an organ, and an organism.

The delay can be greater than about 10 nanoseconds. The delay can be greater than between about 10 nanoseconds and about 20 nanoseconds.

The absorption wavelength can be generated by a pulsed laser. The absorption wavelength can be between about 450 nm and about 650 nm or between about 900 nm and about 1300 nm. The absorption wavelength can be between about 450 nm and about 650 nm or between about 850 nm and about 1350 nm.

Another aspect of the invention provides a non-transitory computer readable medium containing program instructions executable by a processor. The computer readable medium includes: (a) program instructions that apply an absorption wavelength to an object of interest impregnated with fluorescent nanodiamonds; and (b) program instructions that, after a delay of at least at least about 6 nanoseconds, acquire a fluorescent image of the object of interest.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the following views.

FIG. 3 depicts an example of pixel-by-pixel subtraction of a second fluorescent image from a first fluorescent image according to an embodiment of present subject matter.

FIG. 7A depicts the energy level diagram of negatively-charged nitrogen vacancy (NV) centers. FIG. 7B depicts a field of view containing FNDs. FIG. 7C depicts the intensity modulation of the FND depicted in FIG. 7A upon application of a modulating magnetic field with 0.1 Hz frequency and 100 Gauss amplitude.

DEFINITIONS

The present subject matter is most clearly understood with reference to the following definitions:

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "background-free image" refers to an image having a sufficiently high signal-to-noise ratio (SNR) such that the fluorescence of fluorescent nanodiamonds can be distinguished from the fluorescence of background elements such as endogenous proteins. Suitable SNRs include those greater than about 1:1, about 1.5:1, about 2:1, about 3:1, about 4:1, about 5:1, about 6:1, about 7:1, about 8:1, about 9:1, and about 10:1.

As used herein, the terms "comprises," "comprising," "containing," "having," and the like can have the meaning ascribed to them in U.S. patent law and can mean "includes," "including," and the like.

As used herein, the term "fluorescent image" refers to an image representing one or more fluorescent emissions. For example, the fluorescent emissions can be between about 625 nm and about 825 nm. Fluorescent images are typically obtained typically obtained by applying an absorption wavelength to an object of interest and simultaneously or after a delay, capturing an image of fluorescent emissions. Fluorescent images can be obtained using a variety of devices including fluorescent microscopes. The fluorescent image can, in some embodiments, be a two-dimensional image consisting of a plurality of pixels, each of which can be a numerical representation of the intensity of fluorescence as at particular location.

Figure 1:
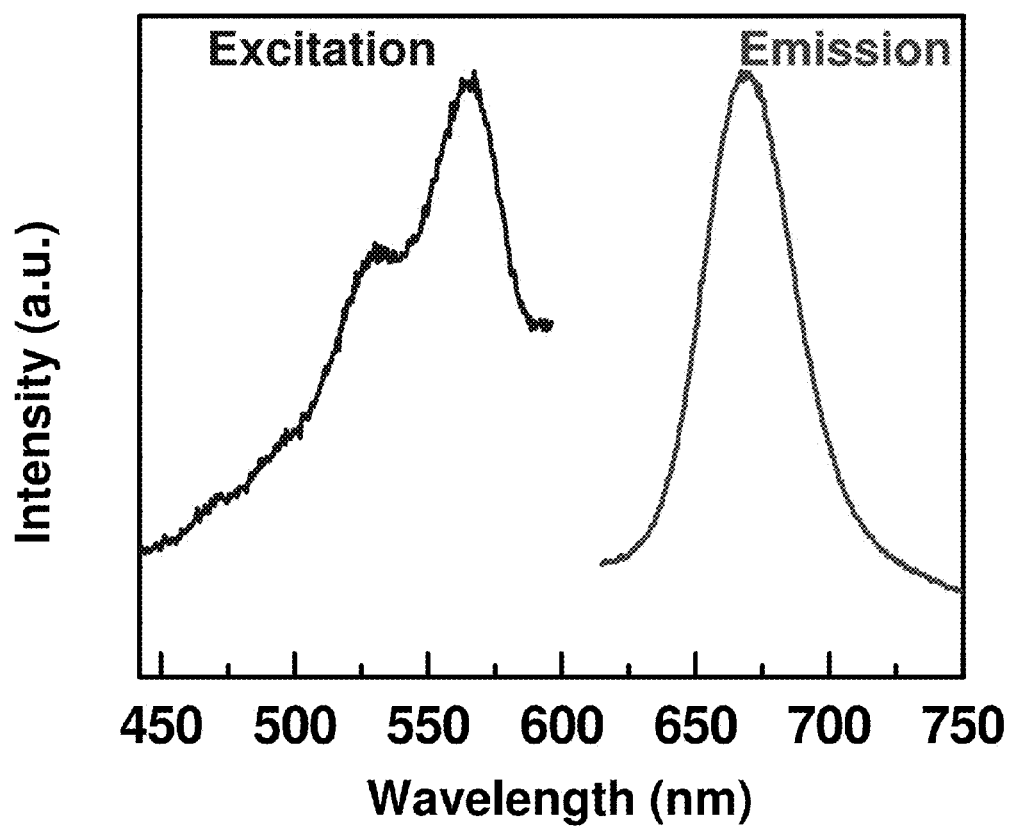
FIG. 1 depicts the absorption (excitation) and emission spectrums of diamond nitrogen-vacancy centers.

As used herein, the term "fluorescent nanodiamond" (abbreviated as "FND") refers to nanodiamonds that exhibit fluorescence when exposed to an appropriate absorption (excitation) spectrum. This fluorescence can be caused by the presence of nitrogen-vacancy (NV) centers, where a nitrogen atom is located next to a vacancy in the nanodiamond. The absorption (excitation) and emission spectrums of silica-coated FNDs having a diameter of about 100 nm are depicted in FIG. 1. The absorption (excitation) spectrum generally lies between about 450 nm and about 600 nm with an excitation peak at about 565 nm. (FNDs can also be excited by a two-photon process in the wavelength region between about 900 nm and about 1300 nm.) The emission spectrum generally lies between about 625 nm and about 750 nm, with an emission peak at about 700 nm. (In the working examples described herein, the samples were excited at 575 nm and a PTI fluorometer was used to obtain the excitation spectra.)

As used herein, the term "nanodiamond" refers to diamonds having a largest dimension of less than about 100 nm. For example, the largest dimension of a nanodiamond can be less than: about 100 nm, about 90 nm, about 80 nm, about 70 nm, about 60 nm, about 50 nm, about 40 nm, about 30 nm, about 20 nm, about 20 nm, about 10 nm, and the like.

As used herein, the term "object of interest" refers to any object of which a fluorescent image is desired. An object of interest can be a biological target, for example, a living organism or a sample of an organism. The object of interest can be an organism, one or more organs, one or more tissues, and/or one or more cells. Although the examples described herein are largely directed toward biological imaging, FNDs and the methods described herein can be used to increase the single to noise in any imaging application in which a modulated magnetic field can be applied to the sample. For example, FNDs and the methods described herein can be used to image and study flow or morphology in a high background environment.

Unless specifically stated or obvious from context, the term "or," as used herein, is understood to be inclusive.

By "specifically binds" is meant recognition and binding to a target (e.g., polypeptide, cell, surface antigen, and the like), but which does not substantially recognize and bind other molecules in a sample, for example, a biological sample.

The term "subject" as used herein, refers to any organism that is suitable for being imaged by the methods described herein. Such organisms include, but are not limited to, human, dog, cat, horse, cow, sheep, goat, mouse, rat, guinea pig, monkey, avian, reptiles, bacteria, fungi, viruses, and the like.

The term "tissue" as used herein, refers to a subject's body. Nonlimiting examples of tissues include tissues from organs such as brain, heart, lung, liver, stomach, pancreas, colon, rectum, intestines, blood vessels, arteries, and the like.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE PRESENT SUBJECT MATTER

Nitrogen vacancy centers in nanodiamonds are unique fluorescent sources that do not photobleach or blink. Remarkably, the fluorescence intensity of these fluorescent nanodiamonds can be modulated by a magnetic field of moderate strength (~0.01 T). Furthermore the fluorescence lifetime of nanodiamonds (~10-20 ns) is longer than the lifetime (≤5-6 ns) of most fluorophores that contribute to autofluorescence. Both of these properties of nanodiamonds can be used to achieve background-free imaging. The modulation of the fluorescence intensity with applied magnetic field is a unique feature of the fluorescent nanodiamonds, which in combination with their other features enables a number of novel imaging applications. Background-free imaging is one of these applications.

The discovery allows background-free imaging of fluorescent nanodiamonds in tissue samples and in vivo, where conventional imaging is difficult due to background fluorescence. We present several techniques to reduce or eliminate background florescence by exploiting properties of the fluorescent nanodiamonds. In particular, magnetic field modulation of the fluorescence intensity offers a simple, robust, and easily adaptable method to obtain background-free imaging in a variety of imaging modalities, i.e., fluorescence microscopy, confocal fluorescence microscopy, and wide-field fluorescence animal imaging.

In one embodiment of the present subject matter, subtracting an image acquired with the magnetic field from one without the field collected under otherwise identical conditions eliminates constant background fluorescence while highlighting the diamond fluorescence that is specifically reduced in one image.

In another embodiment, the field is modulated sinusoidally while images are acquired. Phase-sensitive detection of the modulated intensity can then be achieved by post-processing for camera-based imaging or through lock-in techniques in confocal-based imaging. This technique could be adapted for use in wide-field and confocal imaging systems. Importantly, this technique makes use of conventional continuous wave illumination.

Yet another embodiment makes use of the long excited state lifetime of the fluorescent nanodiamonds to reject shorter-lived background fluorescence. This technique relies on a pulsed laser and time-gated or lifetime imaging. Fluorescent nanodiamonds can be imaged with two-photon approaches, facilitating these lifetime-based background rejection techniques.

Methods of Producing Background-Free Image by Subtraction

Figure 2:
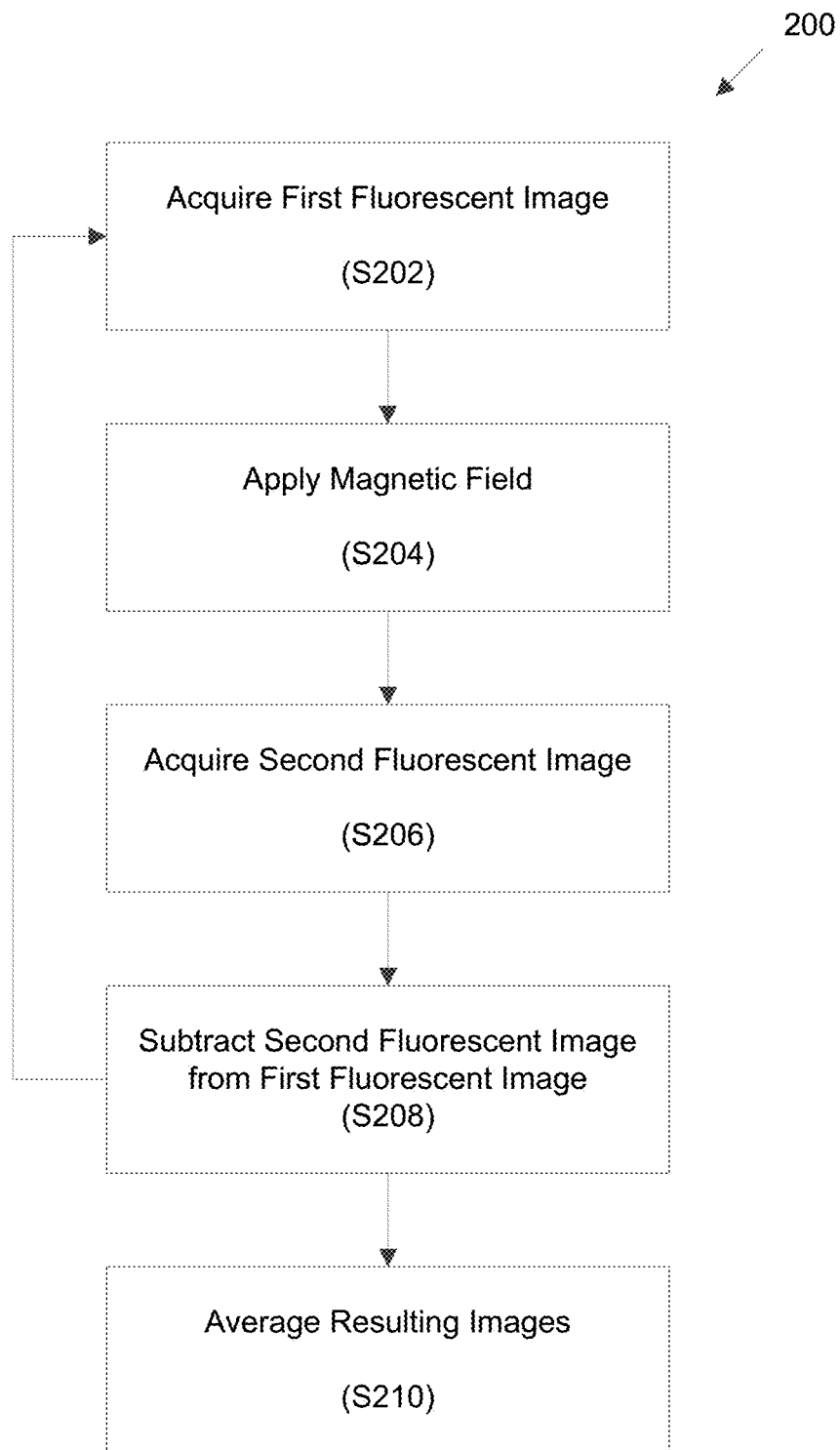
FIG. 2 depicts an imaging method according to an embodiment of the present subject matter.

Referring now to FIG. 2, an imaging method 200 is provided.

In step S202, a first fluorescent image is acquired of an object of interest impregnated with fluorescent nanodiamonds. The fluorescent image can be acquired using conventional fluorescent imaging devices as described herein.

In step S204, a magnetic field is applied to the fluorescent nanodiamonds in order to decrease fluorescence of the fluorescent nanodiamonds. The magnetic field can be applied, for example, with a permanent magnet or an electromagnet. The magnetic field modulates the fluorescence intensity of the fluorescent nanodiamonds such that the fluorescence intensity of the fluorescent nanodiamonds is less than in the first fluorescent image.

In step S206, a second fluorescent image is acquired of the object of interest. Preferably, the second fluorescent image has identical parameters to the first fluorescent image other than the decreased fluorescence intensity of fluorescent nanodiamonds as a result of the application of the magnetic field. The second fluorescent image is acquired while the magnetic field is applied.

Figure 3:
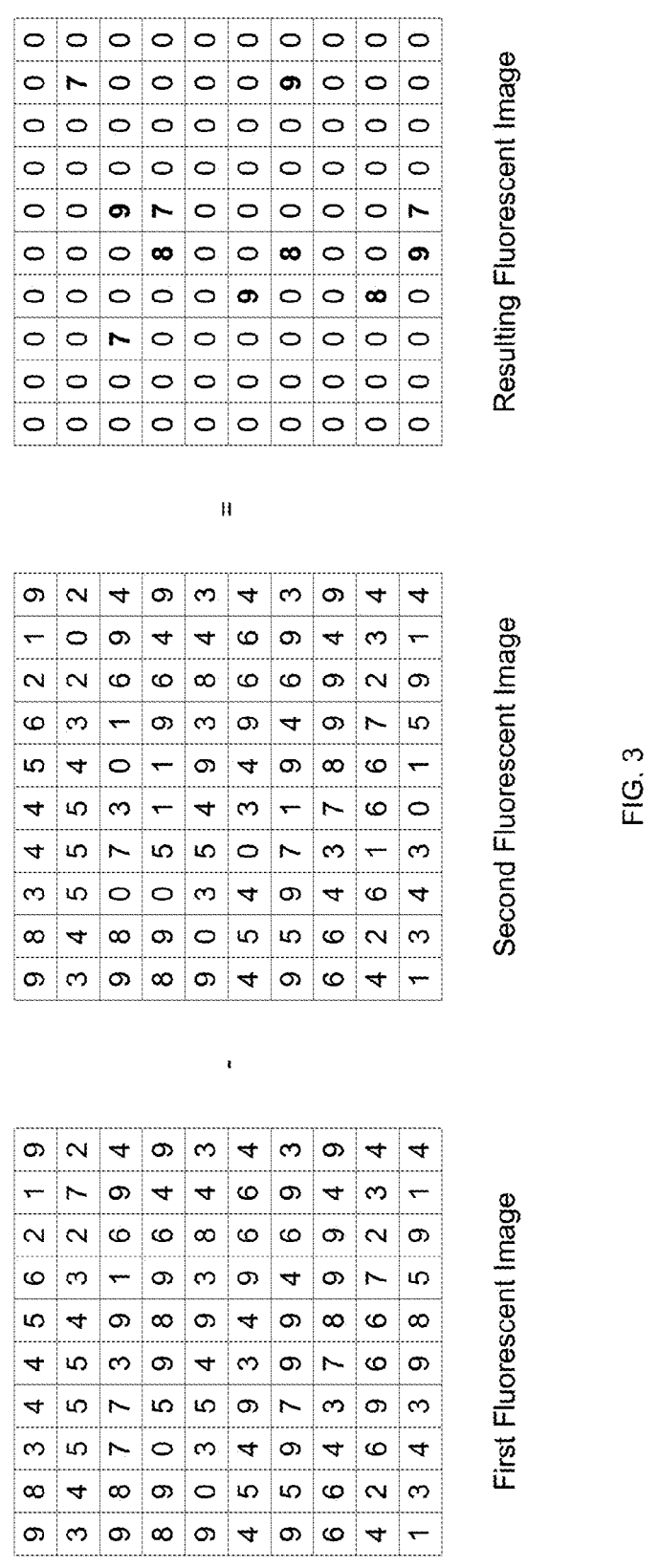

In step S208, the second fluorescent image is subtracted from the first fluorescent image to produce a resulting image. The subtraction can be performed on a pixel-by-pixel basis. For example, as shown conceptually in FIG. 3, a second 10×10 pixel fluorescent image can be subtracted from a first 10×10 pixel fluorescent image to produce a resulting image. Because the only difference between the first fluorescent image and the second fluorescent image is the modulation of fluorescent nanodiamonds, the background fluorescence (e.g., from endogenous proteins) will be canceled out by the subtraction to produce a background-free fluorescent image.

Pixel-by-pixel subtraction can be performed manually or can be automated. A variety of commercially-available computer programs can perform image subtraction including, for example, MATLAB® software available from The MathWorks, Inc. of Natick, Mass. and IMAGEJ software available from the National Institutes of Health at http://rsbweb.nih.gov/ij/.

In step S210, steps S202-S208 are repeated a plurality of times (e.g., greater than 10) and the resulting images are averaged on a pixel-by-pixel basis to improve the imaging quality.

Methods of Producing Background-Free Images Using Lock-In Techniques

Figure 4:
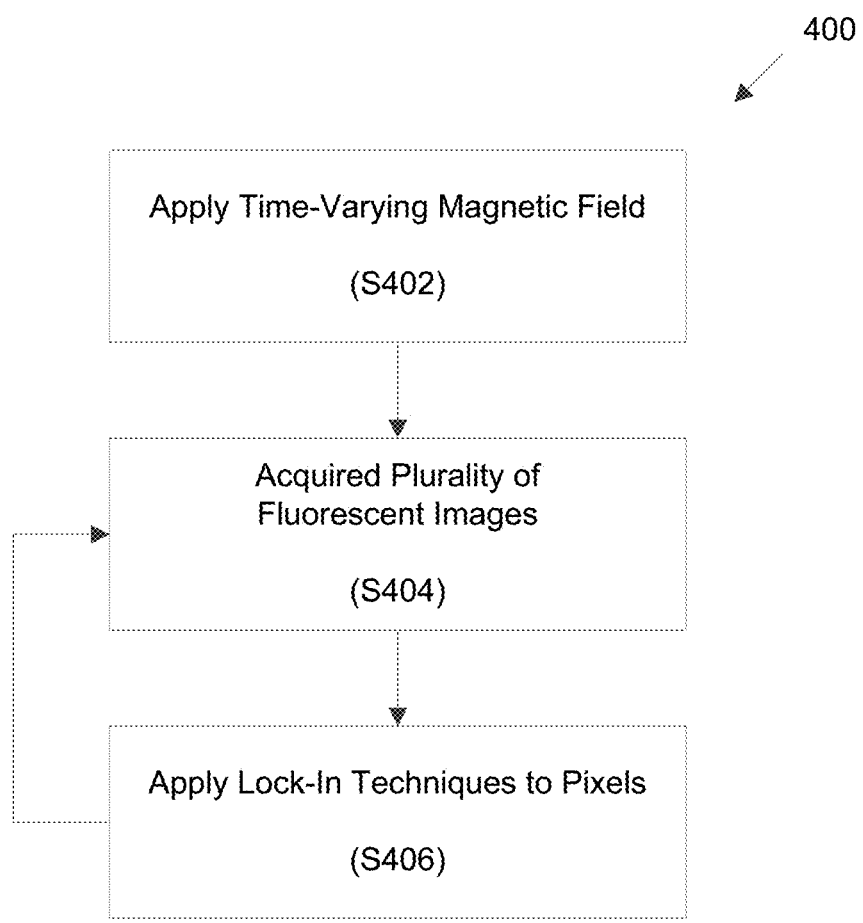
FIG. 4 depicts an imaging method according to another embodiment of the present subject matter.

Referring now to FIG. 4, another imaging method 400 is provided.

In step S402, time-varying magnetic field is applied to an object of interest impregnated with fluorescent nanodiamonds to modulate the fluorescence of the fluorescent nanodiamonds. The time-varying magnetic field can vary cyclically. For example, the magnitude of the magnetic field can vary sinusoidally. The magnetic field can be varied by modulating the current applied to an electromagnet or by modulating the distance between the magnet (either a permanent magnet or an electromagnet) and the object of interest.

In step S404, a plurality of fluorescent images of the object of interest are acquired. Preferably, the plurality of fluorescent images are captured at a plurality of points within a cycle. The sampling can occur at regular or irregular intervals and can, but need not, be matched to the frequency of the phase-modified magnetic field. The plurality of fluorescent images can be acquired pixel-by-pixel using a point imager such as a confocal microscope or multiple pixels at a time using a wide-field imager.

In step S406, the fluorescence intensity of each pixel is calculated using a lock-in technique. Lock-in techniques multiply the fluorescence intensity in each pixel of the plurality of fluorescent images by the amplitude of the magnetic field at the time of each respective fluorescent image and then calculate the intensity of the appropriately filtered or processed resulting products. All background fluorescence will not fluctuate in phase with the magnetic field modulation over all images and will therefore average to zero. The fluorescence intensity of the fluorescent nanodiamonds will vary in phase with the magnetic intensity and, therefore, average to half of the amplitude of the magnetic intensity.

Lock-in techniques are described in publications such as Richard Burdett, "Amplitude Modulated Signals—The Lock-in Amplifier," in *Handbook of Measuring System Design* (2005) and Stanford Research Systems, Inc., "About Lock-In Amplifiers: Application Note #3," available at http://www.thinksrs.com/downloads/PDFs/Application-Notes/AboutLIAs.pdf. Generally speaking, single-pixel inputs obtained from point detectors can processed directly by conventional lock-in amplifiers available from suppliers such as Stanford Research Systems, Inc. of Sunnyvale, Calif., while algorithms can be written using software such as MATLAB® to step through each set of corresponding pixels in a series of fluorescent images and perform a lock-in technique to produce a resulting background-free image.

If the fluorescent images are acquired pixel-by-pixel, a lock-in technique can be applied for that particular pixel before acquiring another pixel. If the images are acquired using a wide-field imager, a lock-in technique can be applied on a pixel-by-pixel basis after all images are acquired.

Figure 5:
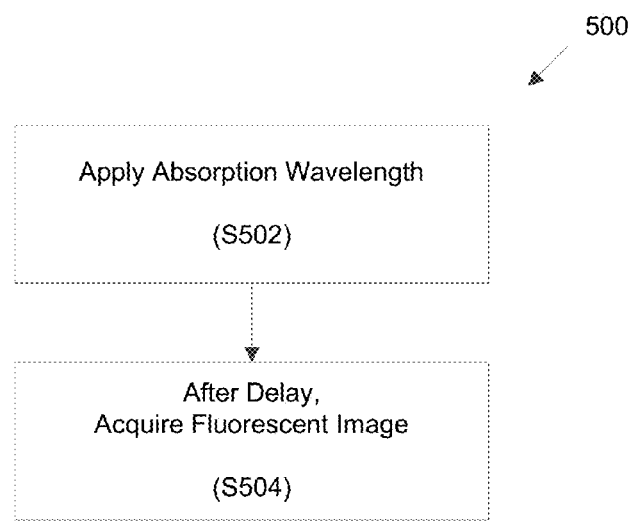
FIG. 5 depicts an imaging method according to another embodiment of the present subject matter.

Method of Producing a Background-Free Image by Exploiting Excited State Lifetime of FNDs Referring now to FIG. 5, another imaging method 500 is provided.

In step S502, an absorption wavelength (e.g., a brief pulse of 5 ns or less) is applied to an object of interest impregnated with fluorescent nanodiamonds. This absorption wavelength will excite FNDs, but may also excite various background elements such as endogenous proteins.

In step S504, after a delay of at least at least about 6 nanoseconds, acquiring a fluorescent image of the object of interest. After 6 nanoseconds, most (if not all) background fluorescence will have dissipated, while the FNDs continue to emit photons. Thus, a background-free image can be captured without the need for the image processing algorithms described above.

Computer Implementation of Methods

Figure 6:
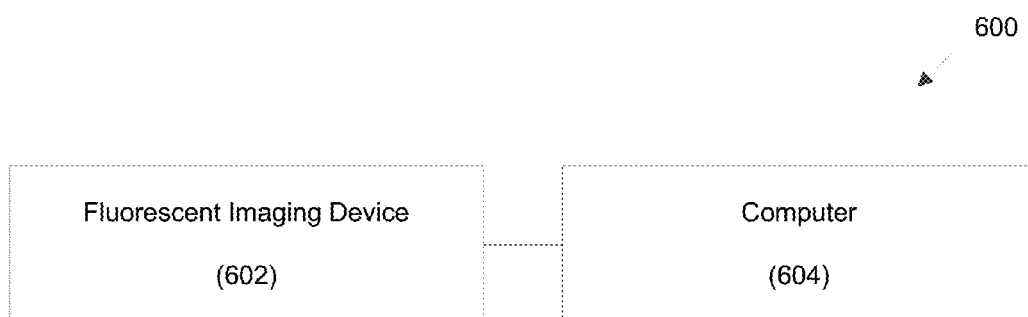
FIG. 6 depicts an imaging system according to an embodiment of the present subject matter.

Referring now to FIG. 6, the methods described herein can be implemented in hardware and/or software. For example, FIG. 6 depicts a system 600 including a fluorescent imaging device 602 such as a fluorescent microscope and a computer 604. The fluorescent imaging device 602 can include an excitation light source, an image sensor (e.g., including a charge-coupled device (CCD), complementary metal-oxide-semiconductor (CMOS) chip, photomultiplier tube (PMT), or avalanche photodiode (APD)), one or more lenses, and a filter adapted to block undesired wavelengths. The computer 604 can be a special-purpose or general-purpose computer can be communicatively coupled with the fluorescent imaging device 602 via communication standards such as parallel or serial ports, Universal Serial Bus (USB), USB 2.0, Firewire, Ethernet, Gigabit Ethernet, and the like.

As understood by those of skill in the art, computer 604 can include various components such as a display device, a processor, and/or a storage device.

Display device can be any device capable of displaying graphics and/or text. Examples of display devices include a cathode ray tube (CRT), a plasma display, a liquid crystal display (LCD), an organic light-emitting diode display (OLED), a light-emitting diode (LED) display, an electroluminescent display (ELD), a surface-conduction electron-emitter display (SED), a field emission display (FED), a nano-emissive display (NED), an electrophoretic display, a bichromal ball display, an interferometric modulator display, a bistable nematic liquid crystal display, and the like.

Processor is an electronic device (also known as a central processing unit or microprocessor) capable of executing instructions stored as hardware and/or software. Suitable processors are available from manufacturers such as Intel Corporation of Santa Clara, Calif. or Advanced Micro Devices (AMD) of Sunnyvale, Calif.

Storage device can include persistent storage devices such as magnetic media (e.g. tapes, disks), optical media (e.g. CD-ROM, CD-R, CD-RW, DVD, HD DVD, BLU-RAY DISK®, Laserdisk), punch cards, and the like. Storage device can also include temporary storage devices known as memory (e.g., random access memory).

Motion Correction of Movies

In some embodiments, motion correction is applied to compensate for motion in the camera and/or the subject. For example, motion correction can be applied to a time series of images to correct for in-plane motion at the sub-pixel level.

In one embodiment, a non-rigid deformation map is calculated pairwise between each image and a common reference image using an optical flow method, which iteratively maximizes the local cross-correlation image subsets at different resolutions. The initial time frame can be chosen as a common reference for both images series acquired with external field ON and OFF in order so that the ON and OFF images are co-registered. A subpixel spline based interpolation can be used for application of the non-rigid deformation to minimize loss of spatial resolution. Following motion correction, the time series of images can be averaged to reduce random fluctuation due to noise thereby creating an average image for the ON and OFF. A difference image between ON and OFF motion corrected averages can be used to analyze the contrast of the probe signal by subtraction of the background tissue. This signal from the nanodiamond can then be overlaid on the starting image.

Fluorescent Nanodiamonds and Compositions Thereof

As described herein, the present invention relates to use of fluorescent nanodiamonds to image an object of interest. Fluorescent nanodiamonds suitable for use in the present invention and methods for making such fluorescent molecules are well-known in the art. See, e.g., *Nanodiamonds: Applications in Biology and Nanoscale Medicine* (D. Ho ed., Springer 2009); *Molecular Imaging* (R. Weissleder et al. eds., 2010); *Medical Nanotechnology and Nanomedicine (Perspectives in Nanotechnology)* (H. F. Tibbals ed., CRC Press 2010); *Molecular Fluorescence* (B. Valeur ed., Wiley-VCH 2012); *Introduction to Nanomedicine and Nanobioengineering* (*Wiley Series in Biomedical Engineering and Multi-Disciplinary Integrated Systems*) (P. N. Prasad ed., Wiley 2012); Yu et al., *J. Am. Chem. Soc.* 127:17604-17605 (2005); Mochalin et al., *Nature Nanotechnology* 7:11-23 (2012); Epstein et al., *Nature Physics* 1:94-98 (2005); Chow et al., *Sci. Transl. Med.* 3:73ra21 (2011); Awschalom et al., *Sci. Am.* 297:84-91 (2007); and Wilson, *Phys. Today* 64:17-18 (2011).

The fluorescent nanodiamonds can be provided as a solution, emulsion, suspension, microsphere, particle, microparticle, nanoparticle, liposomes, and the like.

In aspects of the invention, the fluorescent nanodiamonds are directly contacted with a sample (e.g., when impregnating the fluorescent nanodiamond in a sample in vitro, ex vivo, in situ, etc.). For example, fluorescent nanodiamonds can be impregnated in a sample by injection (e.g., microinjection) or use of a delivery vehicle. Suitable delivery vehicles are well-known in the art. Nonlimiting examples include lipid vesicles or other polymer carrier materials, lipoplexes (see, e.g., U.S. Patent Application Publication No. 2003/0203865; and Zhang et al., *J. Control Release*, 100:165-180 (2004)), pH-sensitive lipoplexes (see, e.g., U.S. Patent Application Publication No. 2002/0192275), reversibly-masked lipoplexes (see, e.g., U.S. Patent Application Publication Nos. 2003/0180950), cationic lipid-based compositions (see, e.g., U.S. Pat. No. 6,756,054; and U.S. Patent Application Publication No. 2005/0234232), cationic liposomes (see, e.g., U.S. Patent Application Publication Nos. 2003/0229040, 2002/0160038, and 2002/0012998; U.S. Pat. No. 5,908,635; and International Publication No. WO 01/72283), anionic liposomes (see, e.g., U.S. Patent Application Publication No. 2003/0026831), pH-sensitive liposomes (see, e.g., U.S. Patent Application Publication No. 2002/0192274; and Australian Publication No. 2003/210303), antibody-coated liposomes (see, e.g., U.S. Patent Application Publication No. 2003/0108597; and International Publication No. WO 00/50008), cell-type-specific liposomes (see, e.g., U.S. Patent Application Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Application Publication No. 2003/0031704), lipid-entrapped molecules (see, e.g., International Publication Nos. WO 03/057190 and WO 03/059322), lipid-encapsulated molecules (see, e.g., U.S. Patent Application Publication No. 2003/0129221; and U.S. Pat. No. 5,756,122), other liposomal compositions (see, e.g., U.S. Patent Application Publication Nos. 2003/0035829 and 2003/0072794; and U.S. Pat. No. 6,200,599), stabilized mixtures of liposomes and emulsions (see, e.g., European Publication No. EP 1 304 160), emulsion compositions (see, e.g., U.S. Pat. No. 6,747,014), and micro-emulsions (see, e.g., U.S. Patent Application Publication No. 2005/0037086).

In some aspects of the invention, the fluorescent nanodiamonds are administered in vivo to a subject (e.g., delivering the fluorescent nanodiamond to a target object within the subject, including, but not limited to, a target cell, tissue, organ, organism, infectious agent, a virus, a bacteria, fungus, a parasite, and the like). When administered to a subject, the fluorescent nanodiamonds can be provided as a pharmaceutical composition including a pharmaceutically acceptable carrier. The term "pharmaceutically acceptable" means approved by a regulatory agency or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is an exemplary carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, and the like. Examples of suitable pharmaceutical carriers are described in "Remington's Pharmaceutical Sciences" by E. W. Martin, the contents of which are hereby incorporated by reference in its entirety.

In embodiments, the imaging agent may be administered through different routes, including, but not limited to, oral, parenteral, buccal and sublingual, rectal, aerosol, nasal, intramuscular, subcutaneous, intradermal, and topical. The term parenteral as used herein includes, for example, intraocular, subcutaneous, intraperitoneal, intracutaneous, intravenous, intramuscular, intraarticular, intraarterial, intrasynovial, intrasternal, intrathecal, intralesional, and intracranial injection, or other infusion techniques. One of ordinary skill in the art would readily understand that the formulation should suit the mode of administration.

Formulations suitable for administration include aqueous and non-aqueous sterile solutions, which may contain antioxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water, immediately prior to use. Extemporaneous solutions and suspensions may be prepared from sterile powders, granules and tablets commonly used by one of ordinary skill in the art.

For oral administration in the form of a tablet or capsule, the fluorescent nanodiamonds can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the fluorescent nanodiamonds can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The fluorescent nanodiamonds used in the methods of the present invention can also be administered in the form of liposome delivery systems. Such delivery systems are well known in the art, and include but are not limited to, unilamellar vesicles, large unilamallar vesicles, and multilamellar vesicles. Liposomes can be formed from a variety of phospholipids, such as cholesterol, stearylamine, or phosphatidylcholines.

The administration of the fluorescent nanodiamonds to a subject can be by a general or local administration route. For example, the fluorescent nanodiamonds may be administered to the subject such that it is delivered throughout the body. Alternatively, the fluorescent nanodiamonds can be administered to a specific organ or tissue of interest.

The fluorescent nanodiamonds should have sufficient emission to assure reliable diagnosis. The amount of fluorescent nanodiamonds to be contacted with a sample or introduced into a subject in order to provide for detection can readily be determined by those skilled in the art. For example, increasing amounts of the fluorescent nanodiamonds can be applied or given to a subject until the fluorescent nanodiamonds are detected by the detection method of choice. In addition, those skilled in the art are also familiar with determining the amount of time sufficient for the fluorescent nanodiamonds to become associated with a target object. The amount of time necessary can easily be determined by introducing a detectable amount of the fluorescent nanodiamonds into a subject and then detecting the fluorescent nanodiamonds at various times after administration.

In some aspects, the fluorescent nanodiamonds can be associated with a molecule that preferentially binds to the target object. Such molecules are well-known in the art, and include but are not limited to target-binding agents having one or more target recognition moieties for the selective binding of the target-binding agents (and fluorescent nanodiamond) to a target molecule. The target recognition moiety is configured to specifically bind to a target molecule of a particular cell, tissue, organ, receptor, surface antigen, organism/infectious agent, and the like.

Examples of target recognition moieties include, but are not limited to, an antigen, ligand, receptor, one member of a specific binding pair, polyamide, peptide, carbohydrate, oligosaccharide, polysaccharide, low density lipoprotein (LDL) or an apoprotein of LDL, steroid, steroid derivative, hormone, hormone-mimic, lectin, drug, antibiotic, aptamer, DNA, RNA, lipid, an antibody, an antibody-related polypeptide, and the like. In embodiments, the targeting moieties are polypeptides, carbohydrates, or lipids. The targeting moieties can also be antibodies, antibody fragments, or nanobodies. In other embodiments, the target recognition moiety can be a molecule or a macromolecular structure (e.g., a liposome, a micelle, a lipid vesicle, or the like) that preferentially associates or binds to a particular tissue, receptor, organism/infectious agent, and the like.

One of ordinary skill in the art would readily understand how to make the fluorescent nanodiamond conjugates contemplated herein. For example, the fluorescent nanodiamonds can be covalently or non-covalently associated with the target binding agent/moiety. See Vaijayanthimalal et al., *Nanomedicine* 4:47-55 (2009); Vaijayanthimalal et al., *Biomaterials* 33: 7794-7802 (2012); Hartmann et al., *Chemistry—A European Journal* 18:21, 6485-6492 (2012); Mochalin et al., *Nat. Nanotechnology* 7:11-23 (2012); Weng et al., *Diamond and Related Materials* 22:96-104 (2012); Alhaddad et al., *Small* 7:3087-3095 (2011); Krueger, *J. Mater. Chem.* 21:12571-12578 (2011); and Liu et al., *Nanoscale*

Research Letters 5:1045-1050 (2010); Rurack, *Supramolecular Chemistry Meets Hybrid (Nano)Materials: A Brief Look Ahead*, pages 689-700 of *The Supramolecular Chemistry of Organic-Inorganic Hybrid Materials* (Wiley, 2010).

In some embodiments, the FNDs are silica-coated FNDs. Methods for creating silica-coated nanodiamonds are described in A. Bumb et al., "Silica encapsulation of fluorescent nanodiamonds for colloidal stability and facile surface functionalization," 135 *Journal of the American Chemical Society* 7815-18 (2013).

WORKING EXAMPLES

Working Example #1

Magnetic Modulation of FND Emission

FIG. 7A depicts the energy level diagram of NV$^-$ centers in diamond showing spin-triplet ($m_s$=0 and $m_s$=±1) ground and excited states as well as the singlet metastable state. NV$^-$ centers can be optically excited over a broad range of wavelengths (450-650 nm) (green arrows). NV$^-$ centers in the $m_s$=±1 sublevels of the excited states have a higher probability to decay via the metastable state (grey dashed arrows) than to the $m_s$=±1 sublevels of the ground state. From the metastable state, NV$^-$ centers predominantly transition to the $m_s$=0 sublevel of the ground state without emitting visible light. Therefore, in the absence of a magnetic field, NV$^-$ centers are rapidly pumped into the $m_s$=0 sublevel of the ground state when excited. This results in an initial increase in fluorescence emission intensity as steady state is reached. In the presence of a magnetic field, the $m_s$=0 and $m_s$=±1 states are mixed, making the decay pathway through the metastable singlet state accessible and therefore decreasing the fluorescence emission intensity.

FIG. 7A depicts a field of view containing FNDs. FIG. 7B depicts the intensity modulation of the FND depicted in FIG. 7A upon application of a modulating magnetic field with 0.1 Hz frequency and 100 Gauss amplitude.

To show magnetic modulation of FND emission, a coverslip was prepared with FNDs. 500 μl of 1 mg/ml poly-L-lysine (PLL) in PBS buffer was mixed with silica-coated FNDs, deposited on a #1 coverslip, and incubated overnight. A flow cell was made using double-sided tape to attach the coverslip to a glass slide.

Movies were obtained using a CARL ZEISS® LSMS LIVE microscope. Each frame of the movie was a scanning confocal image with 250 ms time resolution. A 10× ZEISS® objective with 0.3 NA (EC Plan-Neofluar) was used to introduce the excitation light to stimulate the FNDs and to collect the FND emission. Samples were excited at 532 nm, emission was filtered using a long pass filter LP650 and detected using a photomultiplier tube (PMT).

An electromagnet (APW Company, Item #EM400-12-212, 4.0" Diameter Round Electromagnet) was powered by square wave voltage signal with an amplitude of 0 or 12V and zero offset. The sample was placed ~13 mm away from the face of the magnet, where the magnetic field strength was ~100 Gauss.

Working Example #2

Figure 8A:
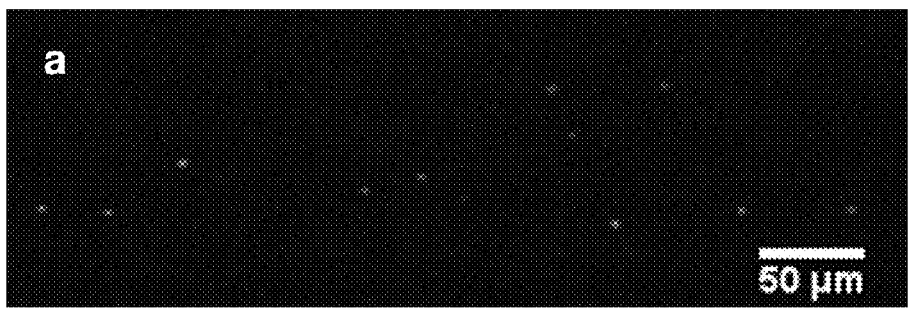
FIG. 8A is a scanning confocal image of FNDs on the surface of a slide.
Figure 8B:
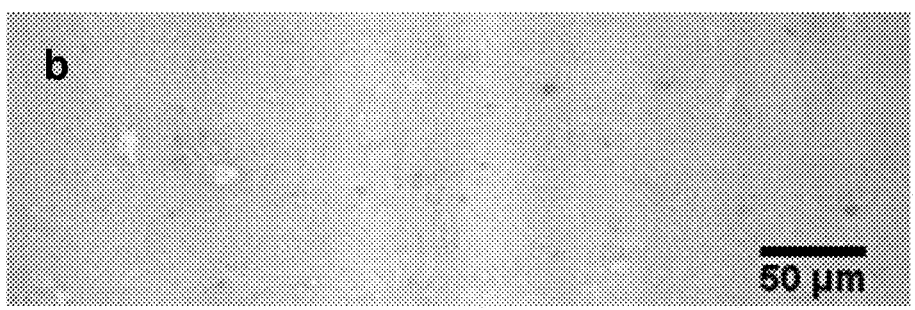
FIG. 8B is a scanning confocal image taken under identical imaging conditions of the same field of view after the addition of ~1 μM ALEXA FLUOR® 647 dye, which has a comparable emission spectrum to that of the FNDs. The fluorescence from the high concentration of ALEXA FLUOR® 647 dye completely obscures the fluorescence of the FNDs.
Figure 8C:
FIG. 8C is a background-free image of the same field of view after processing images in the presence of the high ALEXA FLUOR® 647 dye background (as in FIG. 8B). The difference between pairs of images collected with and without the magnetic field was computed and 1000 of these difference images were averaged together to generate the processed image. Through this processing, images of the diamonds shown in FIG. 8A are recovered from images with high background like FIG. 8B.

Background-Free Imaging by Pairwise Subtraction of Frames with and Without Magnetic Field FIG. 8A is an image of a field of view with ~40 nm FNDs containing ~15 NV$^-$ imaged as in FIG. 7B. FIG. 8B is an image of the same field of view after introducing ~1 μM ALEXA FLUOR® 647 dye solution into the flow cell. This dye has similar emission characteristics as the FNDs so the fluorescence from the FNDs is masked by the background fluorescence of high concentration of the ALEXA FLUOR® 647 dye. FIG. 8C is an image of the same field of view after processing images in the presence of the high ALEXA FLUOR® 647 dye background (as in FIG. 8B). The difference between pairs of images collected with and without the magnetic field was computed and 1,000 of these difference images were averaged together to generate the processed image. Through this processing, images of the diamonds shown in FIG. 8A are recovered from images with high background like FIG. 8B.

Working Example #3

Background-Free Imaging Using Wide-Field Lock-In Detection

Figure 9B:
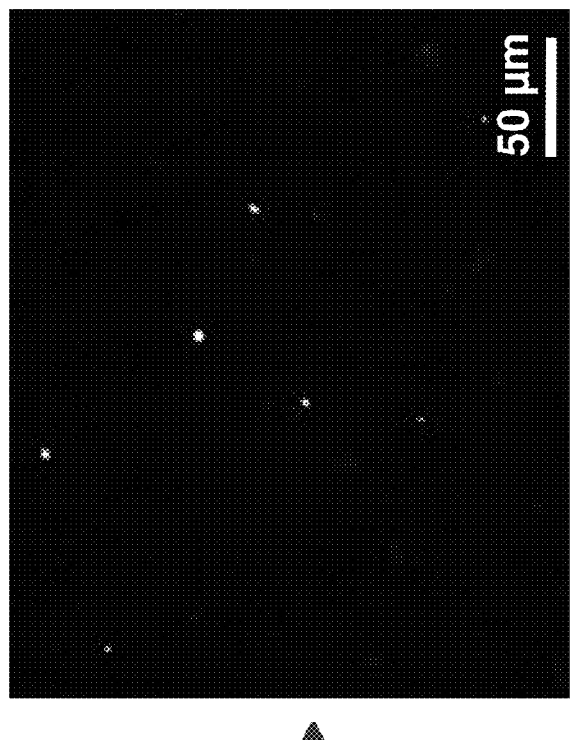
FIG. 9B shows the wide field background-free image after processing the movie pixel-by-pixel using a lock-in algorithm.
Figure 9A:
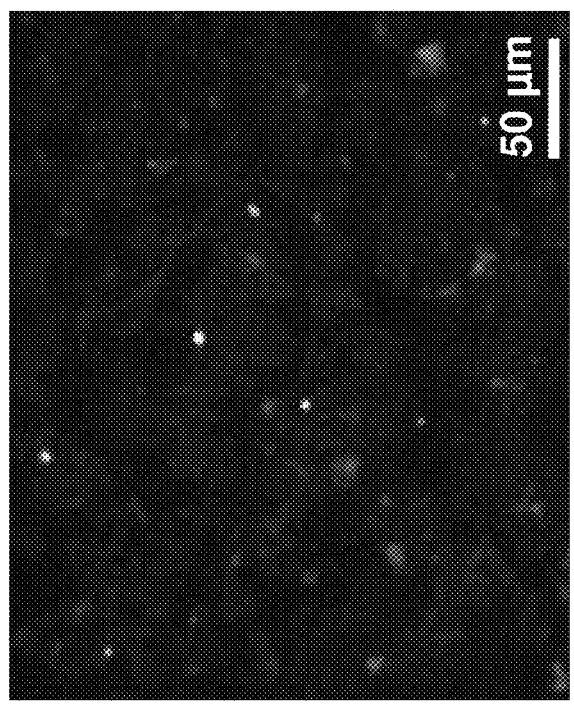
FIG. 9A is a frame of a movie taken by a scanning confocal microscope.

FIG. 9A shows a frame of a movie (1000 frames with time resolution 0.25 s) taken by a scanning confocal microscope. The details of the imaging are identical to those in FIG. 7B above. A modulating magnetic field with 0.1 Hz frequency and 100 Gauss amplitude was applied during the acquisition of the movie.

FIG. 9B shows the wide field background-free image after processing the movie pixel-by-pixel using a lock-in algorithm.

Figure 9C:
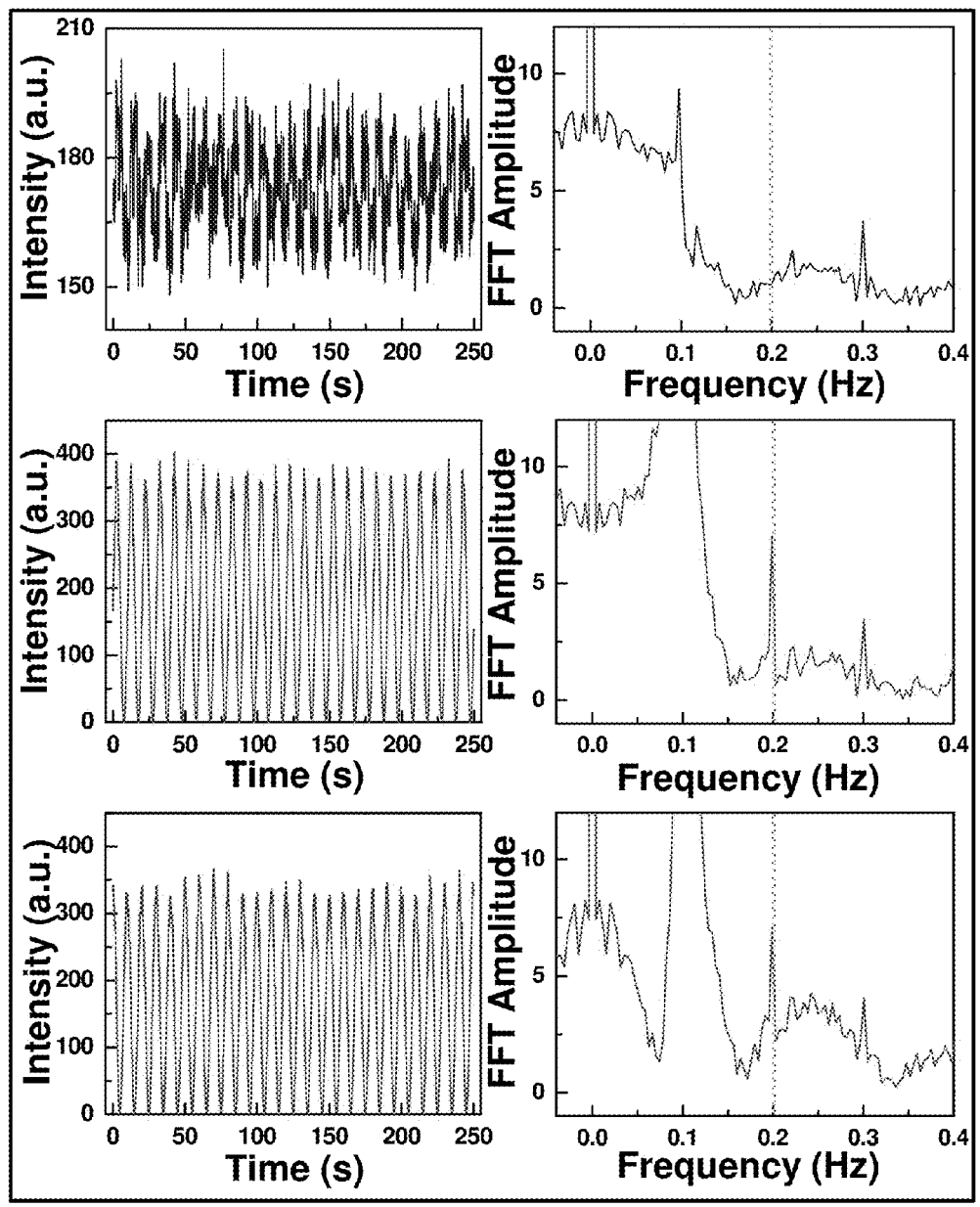
FIG. 9C depicts the application of the lock-in algorithm to a bright pixel (horizontal coordinate, x=109 and vertical coordinate, y=111 from the top left corner of the image in FIG. 9A) corresponding to a FND.

FIG. 9C depicts the application of the lock-in algorithm to a bright pixel (horizontal coordinate, x=109 and vertical coordinate, y=111 from the top left corner of the image in FIG. 9A) corresponding to a FND. The top left panel of FIG. 9C illustrates the pixel values as a function of time. The top right panel of FIG. 9C illustrates the fast Fourier transform (FFT) as a function of frequency. The middle left panel of FIG. 9C depicts the pixel values from the top left panel multiplied by a reference sine wave $1+\sin(2\pi*0.1*t)$. The middle right panel of FIG. 9C depicts the corresponding FFT. The bottom left panel of FIG. 9C shows the pixel values multiplied with a reference cosine wave $1+\cos(2\pi*0.1*t)$. The bottom right panel of FIG. 9C depicts the corresponding FFT.

Figure 9D:
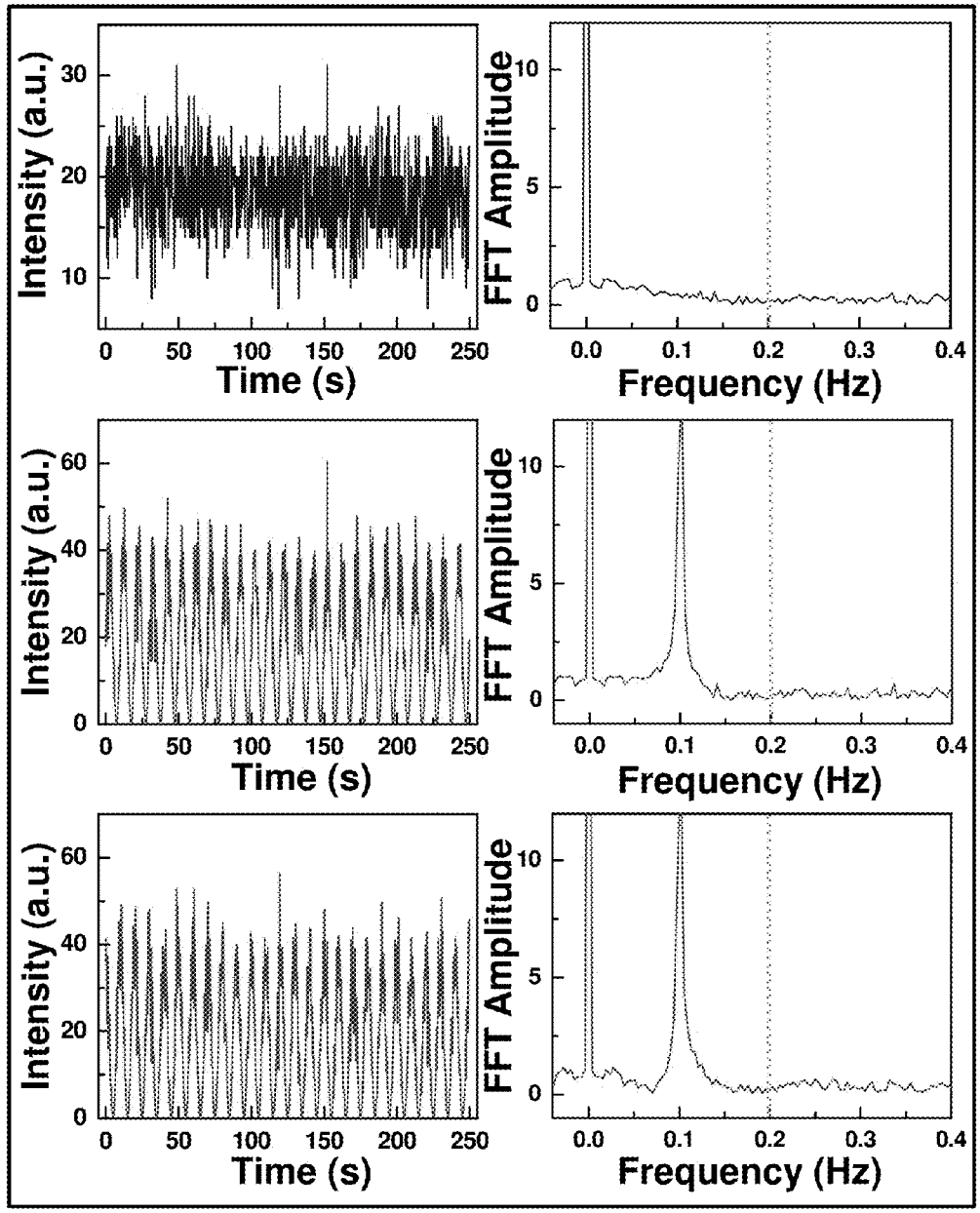
FIG. 9D illustrates the same lock-in algorithm applied to a dark pixel (horizontal coordinate, x=137 and vertical coordinate, y=107 from the top left corner of the image in FIG. 9A) corresponding to the background.

FIG. 9D illustrates the same lock-in algorithm applied to a dark pixel (horizontal coordinate, x=137 and vertical coordinate, y=107 from the top left corner of the image in FIG. 9A) corresponding to the background.

Referring to both FIGS. 9C and 9D, vertical dashed lines at 0.2 Hz are guides to indicate the values at twice the reference frequency. Means of three points around 0.2 Hz in the sine and cosine FFTs were calculated for each pixel. The background-free image in FIG. 9B corresponds to the sine and cosine means added in quadrature, i.e, $i=\sqrt{i\cos^2+i\sin^2}$, where i is the mean intensity and i cos and i sin correspond to the means calculated from the FFT of the signal multiplied by the cosine and sine functions respectively. Means of the pixel values over 1000 frames were 173 and 18 for the pixels at (109,111) and (137,107) before applying the lock-in algorithm giving a signal-to-noise ratio of ~10. Means of the FFT amplitudes for three points around 0.2 Hz are 21.42 and 0.28 for the pixels at (109,111) and (137,107) after applying the lock-in algorithm giving a signal-to-noise ratio of ~77. Thus the lock-in algorithm increased the signal to noise ratio by a factor of ~8. Computations were implemented in MATLAB® software.

Working Example #4

Figure 10C:
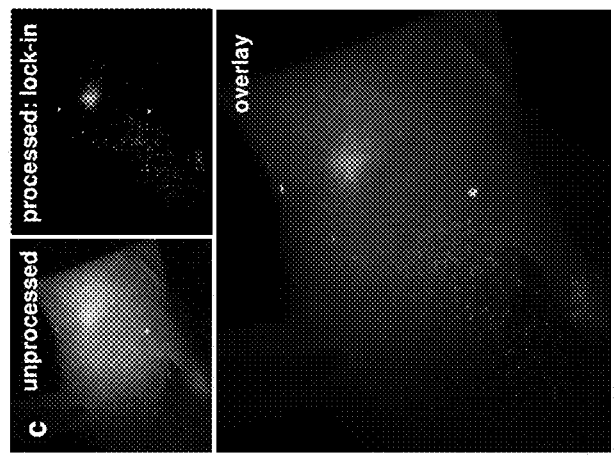
FIG. 10C depicts the same images as FIG. 10B obtained with the wide-field lock-in technique.
Figure 10B:
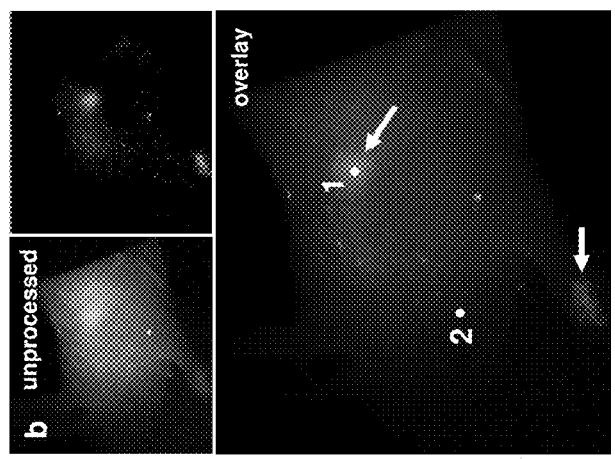
FIG. 10B shows the same mouse imaged with the pairwise image subtraction technique. The lymph node is clearly visible in the processed image (top right) that was produced by pairwise subtraction of fluorescence images (top left) with the magnetic field on and off.
Figure 10A:
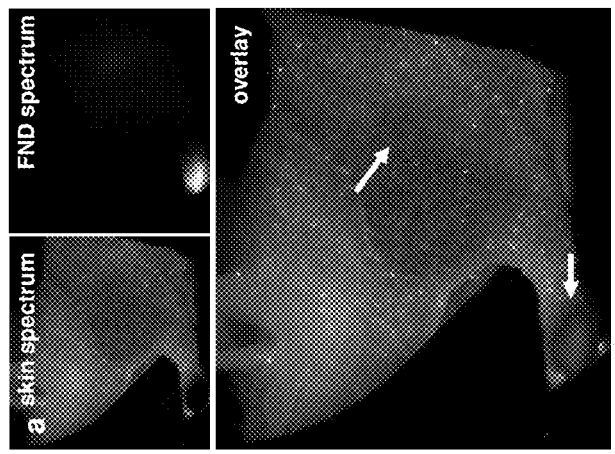
FIG. 10A depicts the fluorescence image acquired with conventional spectral unmixing techniques of the forequarters of a mouse after injection of FNDs. The image is an overlay of the background channel (top left) and the FND channel (top right). The site of injection of the FNDs is visible in the composite but the lymph node cannot be distinguished.
Figure 10D:
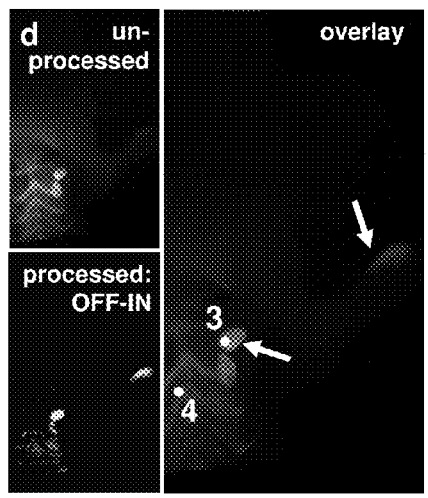
FIG. 10D depicts an image of the opened mouse chest cavity obtained with pairwise subtraction background free detection. The lymph node and the point of initial injection (white arrows) are clearly visible.
Figure 10E:
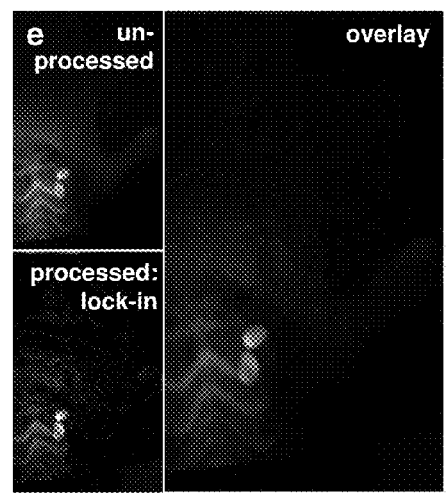
FIG. 10E depicts the same image as FIG. 10D obtained with wide-field lock in background free detection.
Figure 10F:
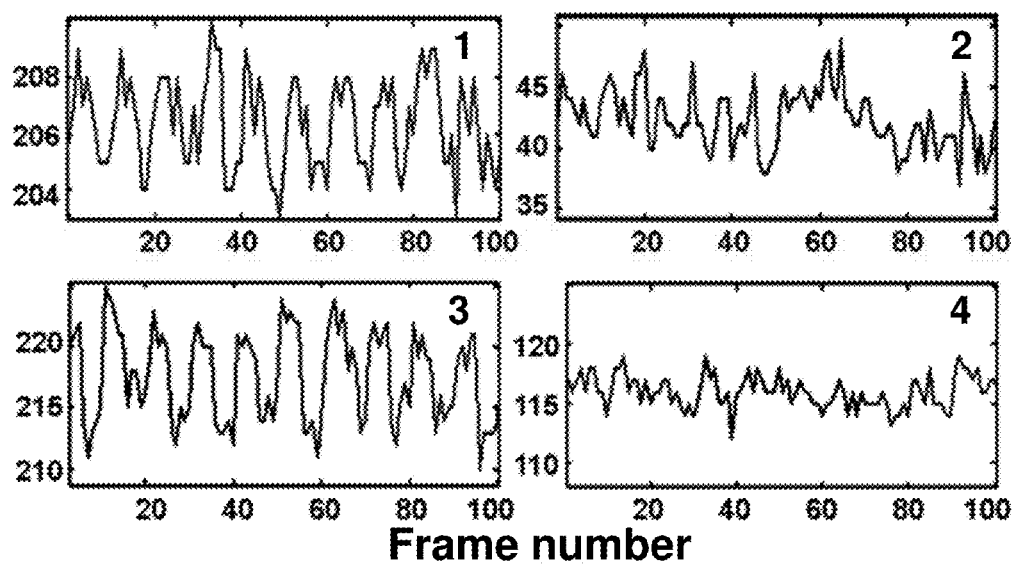
FIG. 10F depicts the intensity as a function of time for points in the images where there are FNDs (1 and 3) and two background spots (2 and 4). The location of the four points are indicated on the images in FIGS. 10B and 10D.

Background-Free Imaging of Sentinal Lymph Node In Vivo Using Wide Field Pairwise Image Subtraction and Lock-In Detection FIG. 10A depicts an image of the forequarters of a mouse obtained using conventional spectral unmixing methods to separate the emission of the FNDs (top right inset, red in overlay) from background fluorescence (top left inset, white in overlay). FNDs were not detected through the skin in the draining axillary lymph node. FIG. 10B depicts an image of the same mouse obtained by averaging 475 pairwise-subtracted images with and without the magnetic field. The processed image (top right inset, red in overlay) was overlaid on an unprocessed image obtained with the magnetic field off (top left inset, white in overlay). The white arrows point to the injection site in the footpad and the location of the auxiliary (sentinel) lymph node. Signal from the FNDs in the lymph node is clearly detected. FIG. 10C depicts an image obtained by lock-in detection of emission from FNDs from the same images used to generate FIG. 10B using the algorithm described in FIG. 9 (top right inset, red in overlay) overlaid on the unprocessed image obtained with the magnetic field off (top left inset, white in overlay). FIG. 10D depicts an image of the same mouse's open chest cavity by averaging of images obtained by pairwise subtracting images with and without the magnetic field. The processed image (bottom inset, red in overlay) was overlaid on an unprocessed image obtained with the magnetic field off (top inset, white in overlay). The white arrows point to the injection site in the front footpad and the location of the auxiliary lymph node. FIG. 10E depicts an image obtained from lock-in detection of emission from FNDs from the same images used to generate FIG. 10D (bottom inset, red in overlay) overlaid on the unprocessed image obtained with the magnetic field off (top inset, white in overlay). In the partially dissected mouse, localization of the FNDs to the lymph node can be clearly seen. FIG. 10F depicts the pixel values as a function time corresponding to the selected points in FIG. 10B and FIG. 10D. The pixels selected were over (1) the axillary lymph node and (2) a negative control on the skin in FIG. 10B and (3) the axillary lymph node and (4) a negative control on a rib in FIG. 10D. Signal modulation as a result of the applied magnetic field is clearly visible in the lymph node through the skin, as well as when the chest cavity was opened. Meanwhile, the skin and rib showed random signal as would be expected for the negative control.

Female athymic (nu/nu) mice were purchased from Charles River Laboratories at 4-6 weeks of age and housed in a specific pathogen-free American Association for Laboratory Animal Care approved facility. All experiments were approved by the National Cancer Institute's Animal Care and Use Committee. Mice were anesthetized using gas mixtures of 1.5-2.5% isoflurane in $O_2$ to maintain a respiration rate of ~30 bpm during the injection procedure. A volume of 10 μL of an ~80 mg/mL silica-coated nanodiamond (~100 nm) solution in PBS (pH7.4) was intradermally injected into the front foot pad of each mouse. Previous studies have shown that the primary draining LNs from this injection site are the axillary and lateral thoracic LNs.

At 24 hours post-injection, the mice were sacrificed and optical imaging was performed using a MAESTRO™ CRi spectroscopic optical camera (excitation filter 523 nm, emission filter 675 nm long pass). Images were also taken with magnetic modulation in a UVP® BIOSPECTRUM® Imaging System equipped with a BIOLITE® MultiSpectral Light Source (excitation filter 525 nm, emission filter 650 nm long pass) with additional illumination provided by a green laser (Z-Bolt® #DPSS-100) achieving ~1 mW/cm$^2$ intensity. Each mouse was imaged in the instrument on a non-magnetic stage under which the permanent magnet (Catalog #DZ08-N52, K&J Magnetics) could be slid in and out. Images were captured in series with magnetic fields off and on and movies stitched together in ImageJ software available at http://rsb.info.nih.gov/ij.

Figure 11A:
FIG. 11A is an image of a lymph node (LN) injected with silica-coated FNDs without applied magnetic field.
Figure 11B:
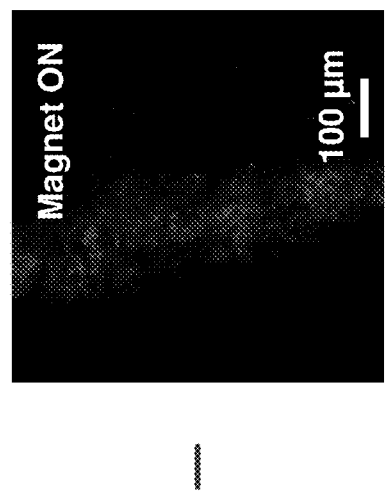
FIG. 11B is an image of the same field of view during application of a magnetic field of ~100 Gauss.
Figure 11C:
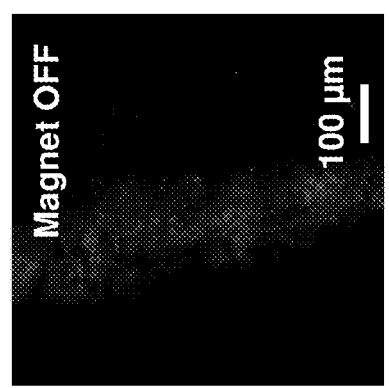
FIG. 11C depicts the sum of 20 subtracted images of FIG. 11B from FIG. 11A. The FNDs are observed as bright spots in the otherwise dark field.
Figure 11D:
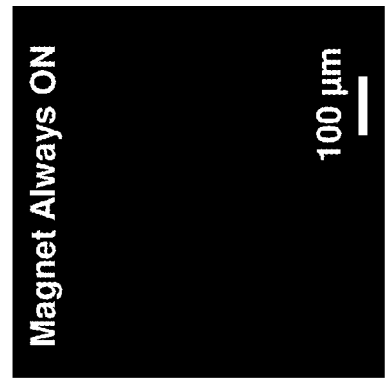
FIGS. 11D and 11E depict the sums of 20 such subtractions when magnetic field was always OFF and ON, respectively.
Figure 11E:

FIG. 11A is an image of a lymph node (LN) injected with silica-coated FNDs without applied magnetic field. FIG. 11B is an image of the same field of view during application of a magnetic field of ~100 Gauss. FIG. 11B was then subtracted from FIG. 11A. FIG. 11C depicts the sum of 20 such subtracted images. The FNDs are observed as bright spots in the otherwise dark field. FIGS. 11D and 11E depict the sums of 20 such subtractions when magnetic field was always OFF and ON, respectively.

Female athymic (nu/nu) mice were purchased from Charles River Laboratories of Wilmington, Mass. at 4-6 weeks of age and housed in a specific pathogen-free American Association for Laboratory Animal Care approved facility. Animals were used between 6 and 8 weeks of age, and experiments were approved by the National Cancer Institute's Animal Care and User Committee. Lymphadenectomy of the axillary and lateral thoracic lymph nodes (LN) of the mice was performed. The excised LN was injected with silica-coated FNDs. The LN was then fixed in 10% formalin for 3 days, washed with PBS, and mounted on a SUPERFROST PLUS® slide (obtained from VWR) using PERMOUNT® medium (obtained from Fisher Scientific) to adhere the coverslip.

Background-free images were obtained by using a Neodymium permanent magnet (obtained from K&J Magnetics of Jamison, Pa.). A CARL ZEISS® LSM5 LIVE microscope was used to obtain the movies. Each frame of the movie was a scanning confocal image with 1 s time resolution. A 10× ZEISS® objective with 0.3 NA (EC Plan-Neofluar) was used to excite the FNDs and collect the FND emission. Samples were excited at 532 nm. Emission was filtered using a long pass filter (bandpass of 560-675 nm) and detected using a PMT.

Working Example #5

Background-Free Imaging Using Fluorescence Lifetime Imaging (FLIM)

Figure 12A:
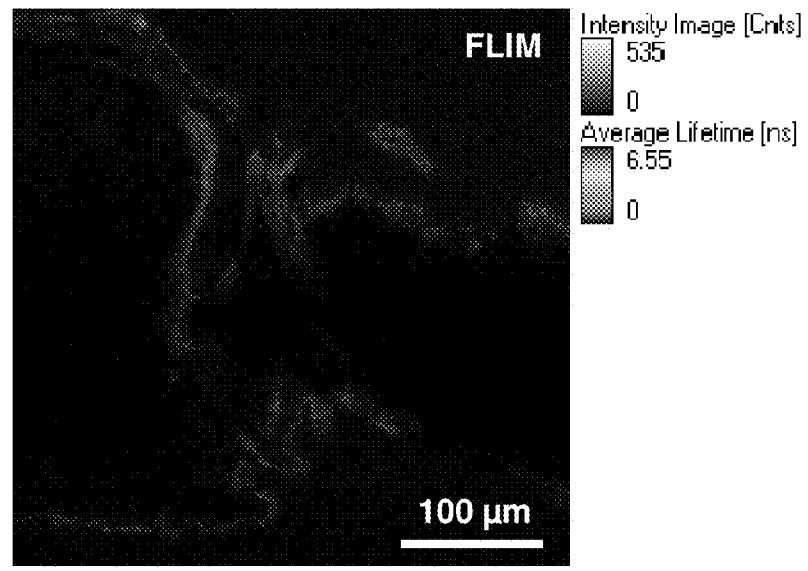
FIG. 12A is a two-photon FLIM image of a different region of the same LN used in FIGS. 11A-11E. Longer lifetimes (indicated by red color) are believed to be due to FNDs, for which the reported lifetimes range from ~10-20 ns.
Figure 12B:
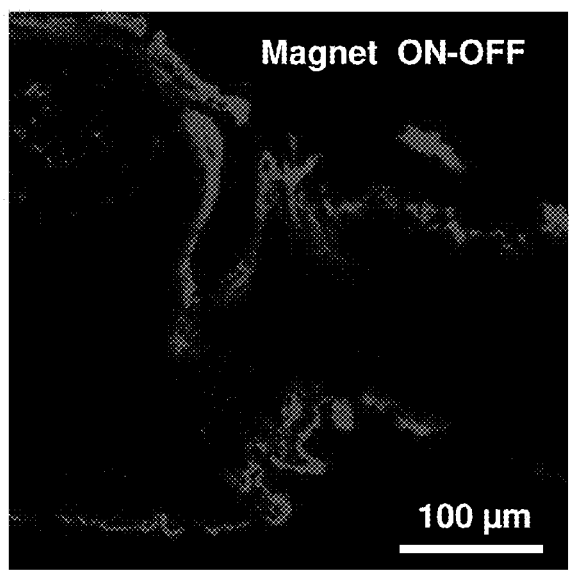
FIG. 12B is a background-free image of the same field of view obtained by subtracting images without and with a magnetic field, and adding 10 such subtractions.

FIG. 12A is a two-photon FLIM image of a different region of the same LN used in FIGS. 11A-11E. Longer lifetimes (indicated by red color) are believed to be due to FNDs, for which the reported lifetimes range from ~10-20 ns. FIG. 12B is a background-free image of the same field of view obtained by subtracting images without and with a magnetic field, and adding 10 such subtractions.

A LEICA® TCS SP5 scanning confocal system was customized to obtain both the fluorescent lifetime imaging microscopy (FLIM) image (FIG. 12A) and the background-free confocal image in which a Neodymium permanent magnet was used to apply the magnetic field (~100 Gauss) (FIG. 12B). For FIG. 12B, 10 subtractions of images with and without magnetic fields were added to obtain the final image. An oil immersion objective (LEICA® HCX PL APO CS 40.0× 1.25 NA Oil UV) was used both to excite and to collect the emission. For the FLIM image, the sample was excited at 930 nm using a SPECTRA-PHYSICS® MAI TAI® laser. For FLIM imaging, emission from the FNDs in the LN was filtered using a band pass filter (BP 607-683 nm) and was detected using a PICOQUANT™ PICOHARP™ 300 Time-Correlated Single Photon Counting (TCSPC) system fitted with single photon avalanche diode (SPAD). For the scanning confocal image (400 Hz scanning speed) of the same field of view (FOV), the sample was excited at 561 nm and the emission was filtered using band pass filter (600-789 nm) and was detected using a PMT.

Conclusion

The present subject matter provides unique, elegant methods that can be easily incorporated with existing microscope or animal imaging systems without coming in contact with the sample. No complicated and error-prone spectral unmixing is necessary. Fluorescence of commonly-used stains and labels cannot be modulated selectively using a magnetic field. Chemical or optical modifications of commonly used labels such as GFP and dyes are possible, but these modifications are difficult to implement, are invasive, and can possibly induce unwanted changes.

EQUIVALENTS

While the present subject matter has been described with reference to the above embodiments, it will be understood by those skilled in the art that various changes can be made and equivalents can be substituted for elements thereof without departing from the scope of the subject matter. In addition, many modifications can be made to adapt a particular situation or material to the teachings of the subject matter without departing from the essential scope thereof. Therefore, it is intended that the subject matter not be limited to the particular embodiment disclosed as the best mode contemplated for carrying out this subject matter, but that the subject matter will include all embodiments falling within the scope of the appended claims.

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, and the like) shown as distinct for purposes of illustration may be incorporated within other functional elements, separated in different hardware or distributed in a particular implementation.

While certain embodiments according to the present subject matter have been described, the present subject matter is not limited to just the described embodiments. Various changes and/or modifications can be made to any of the described embodiments without departing from the spirit or scope of the present subject matter. Also, various combinations of elements, steps, features, and/or aspects of the described embodiments are possible and contemplated even if such combinations are not expressly identified herein.

INCORPORATION BY REFERENCE

The entire contents of all patents, published patent applications, and other references cited herein are hereby expressly incorporated herein in their entireties by reference.

The invention claimed is:

1. An imaging method comprising:
    applying energy to an object, wherein the object is a biological target selected from the group consisting of a cell, a tissue, an organ and an organism, wherein the biological target comprises fluorescent nanodiamonds, and wherein the applied energy consists of optical light and a magnetic field;
    determining the fluorescence intensity of the object; and
    generating an image of the object from the fluorescence intensity.

2. The method of claim 1, wherein applying the magnetic field comprises applying the magnetic field to decrease the fluorescence of the fluorescent nanodiamonds.

3. The method of claim 2, wherein determining the fluorescence intensity comprises:
    acquiring a first fluorescence image of the object;
    acquiring a second fluorescence image while applying the magnetic field; and
    comparing the second fluorescence image to the first fluorescence image to produce a resulting image of the object.

4. The method of claim 3, wherein the image comprises a plurality of pixels and the comparing is performed on a pixel-by-pixel basis.

5. The method of claim 3, further comprising repeating the steps a plurality of times and averaging the resulting images.

6. The method of claim 5, wherein the plurality of times is greater than 10.

7. The method of claim 3, wherein acquiring the first fluorescence image and the second fluorescence image comprises applying the optical light to the object to cause the fluorescent nanodiamonds to fluoresce.

8. The method of claim 1, wherein applying the magnetic field comprises applying a time-varying magnetic field to modulate the fluorescence of the fluorescent nanodiamonds.

9. The method of claim 8, wherein determining the fluorescence intensity comprises:
    acquiring a plurality of fluorescence images of the object, wherein each of the plurality of fluorescence images comprises a plurality of pixels; and
    determining the fluorescence intensity of each of the plurality of pixels using a lock-in technique.

10. The method of claim 9, wherein acquiring the plurality of fluorescence images of the object comprises applying the optical light to the object to cause the fluorescent nanodiamonds to fluoresce.

11. The method of claim 9, wherein acquiring a plurality of fluorescent images comprises using a wide-field camera, a confocal microscope, or a combination thereof.

12. A non-transitory computer readable medium containing program instructions executable by a processor for performing the method of claim 1.

* * * * *